(12) United States Patent
Calio et al.

(10) Patent No.: US 9,339,567 B2
(45) Date of Patent: May 17, 2016

(54) AUTOCLAVABLE BUCKETLESS CLEANING SYSTEM

(71) Applicant: Veltek Associates, Inc., Malvern, PA (US)

(72) Inventors: Rosario S. Calio, Exton, PA (US); Jeffrey Churchvara, Downingtown, PA (US); Arthur Vellutato, Jr., Malvern, PA (US)

(73) Assignee: Veltek Associates, Inc., Malvern, PA (US)

( * ) Notice: Subject to any disclaimer, the term of this patent is extended or adjusted under 35 U.S.C. 154(b) by 244 days.

(21) Appl. No.: 14/175,483

(22) Filed: Feb. 7, 2014

(65) Prior Publication Data

US 2014/0219864 A1    Aug. 7, 2014

Related U.S. Application Data

(60) Continuation of application No. 12/980,122, filed on Dec. 28, 2010, now Pat. No. 8,702,869, which is a division of application No. 12/033,719, filed on Feb. 19, 2008, now abandoned.

(51) Int. Cl.
*B08B 7/00* (2006.01)
*A61L 2/07* (2006.01)
*B08B 3/00* (2006.01)
*B08B 3/02* (2006.01)

(52) U.S. Cl.
CPC ... *A61L 2/07* (2013.01); *B08B 3/00* (2013.01); *B08B 3/026* (2013.01); *Y10T 137/86485* (2015.04)

(58) Field of Classification Search
None
See application file for complete search history.

(56) References Cited

U.S. PATENT DOCUMENTS

| | | |
|---|---|---|
| 3,076,576 A | 2/1963 | Cornelius |
| 3,286,884 A | 11/1966 | Long, Jr. |
| 3,830,632 A | 8/1974 | Guzay |
| 4,114,853 A | 9/1978 | Medvick |

(Continued)

FOREIGN PATENT DOCUMENTS

| | | |
|---|---|---|
| CN | 2817993 Y | 9/2006 |
| CN | 200967463 Y | 10/2007 |

(Continued)

OTHER PUBLICATIONS

Veltek Associates, Inc., "Core2Clean Dual Nozzle Fogger," Model C2C-100-3, Doc No. C2C-2000-D, Rev. Jan. 26, 2004; pp. 1-10.

(Continued)

*Primary Examiner* — Binh X Tran
*Assistant Examiner* — David Cathey, Jr.
(74) *Attorney, Agent, or Firm* — Blank Rome LLP; Peter S. Weissman; Jonathan R. King

(57) ABSTRACT

An autoclavable bucketless cleaning system, including a vessel for storing fluid under pressure, a removably-connectable outlet regulator assembly for dispensing fluid from the vessel, a removably-connectable inlet regulator assembly for pressurizing the vessel, a removably-connectable outlet autoclave stem for installing in the outlet regulator assembly so that steam may pass through the outlet regulator assembly, and a removably-connectable inlet autoclave stem for installing in the inlet regulator assembly so that steam may pass through the inlet regulator assembly.

18 Claims, 3 Drawing Sheets

(56) References Cited

U.S. PATENT DOCUMENTS

| | | | |
|---|---|---|---|
| 4,127,384 | A | 11/1978 | Fahlvik et al. |
| 4,253,684 | A | 3/1981 | Tolbert et al. |
| 4,637,464 | A | 1/1987 | Forgac et al. |
| 4,834,293 | A | 5/1989 | Lichfield |
| 4,889,812 | A | 12/1989 | Guinn et al. |
| 4,898,812 | A | 2/1990 | Aoki et al. |
| 5,016,817 | A | 5/1991 | Ghate et al. |
| 5,045,055 | A | 9/1991 | Gonser et al. |
| 5,064,614 | A | 11/1991 | Reiss et al. |
| 5,277,876 | A | 1/1994 | Wagner |
| 5,424,046 | A | 6/1995 | Smith et al. |
| 5,676,531 | A | 10/1997 | Muscarella et al. |
| 5,678,278 | A | 10/1997 | McBride et al. |
| 5,772,075 | A | 6/1998 | Ash, Jr. et al. |
| 5,906,151 | A | 5/1999 | Firestone et al. |
| 6,216,921 | B1 | 4/2001 | Spruill |
| 6,305,393 | B1 | 10/2001 | Lin |
| 6,379,615 | B1 | 4/2002 | Ogle |
| 6,383,132 | B1 * | 5/2002 | Wimmer .................. A61B 1/12 600/101 |
| 6,455,017 | B1 | 9/2002 | Kasting, Jr. et al. |
| 6,645,429 | B1 | 11/2003 | Raniwala |
| 7,798,373 | B1 | 9/2010 | Wroblewski et al. |
| 2003/0007914 | A1 | 1/2003 | Ongaro |
| 2003/0044312 | A1 | 3/2003 | Takano |
| 2005/0027165 | A1 * | 2/2005 | Rovegno .................. A61B 1/012 600/154 |
| 2007/0264138 | A1 | 11/2007 | Mandell et al. |
| 2008/0292515 | A1 | 11/2008 | Ongaro et al. |

FOREIGN PATENT DOCUMENTS

| | | |
|---|---|---|
| CN | 101090774 A | 12/2007 |
| CN | 201606514 Y | 1/2008 |
| DE | 19711435 C1 | 11/1998 |
| EP | 1287751 A2 | 3/2003 |
| JP | 06049057 A | 2/1994 |
| JP | 2004147967 A | 5/2004 |
| JP | 2004188111 A | 7/2004 |

OTHER PUBLICATIONS

Veltek Associates, Inc., "Validation of the Core2Clean Spray-Mop-Fog Systems," Doc No. C2C-2000-C, Rev. Jan. 26, 2004; pp. 1-26.

Veltek Associates, Inc., "Core 2 Clean Systems [online]"; Jan. 22, 2008, p. 2; pttp://web.archive.org/web/20080122060238/http://www.sterile.com/pages/products/products-cor-2-clean-system.htm.

The State Intellectual Poperty Office of the People's Republic of China; First Office Action and Search Report; 11 pgs., issued Aug. 27, 2012; Application No. 200810161063.X; Applicant: Felteck Associates, Inc.

"The Core 2 Clean® Spray-Mop-Fog System—Operations Manual", The Core2Clean® Systems, Veltek Associates, Inc., Jun. 2003, C2C-2002-F, pp. 1-65.

"Swagelok® Quick Connect Valve Catalogue", Swagelok, www.swagelok.com, Aug. 2005, 12 pages.

Intellectual Property Office of Singapore Search Report for Application No. 2013088190, Feb. 10, 2016, 11 pages.

* cited by examiner

AUTOCLAVABLE BUCKETLESS CLEANING SYSTEM

The present application is a continuation application of U.S. application Ser. No. 12/980,122, filed Dec. 28, 2010, now issued U.S. Pat. No. 8,702,869 B2, which is a divisional application of U.S. application Ser. No. 12/033,719, filed Feb. 19, 2008, now abandoned, the entire contents of which are hereby incorporated by reference as if fully set forth herein.

FIELD OF THE INVENTION

The present invention generally relates to a system for performing cleaning operations in cleanroom environments. More particularly, the present invention relates to a washing system that is bucketless and completely autoclavable and has improved safety features.

BACKGROUND OF THE INVENTION

Many industries require controlled environments that are free from contaminants, such as in surgical suites in hospitals, pharmaceutical and biotechnology manufacturing facilities and laboratories, medical device manufacturing facilities, and micro-electronics manufacturing facilities. Such industries utilize cleanrooms to provide environments in which dust, small particles and other contaminants are reduced. Cleanrooms can function effectively only when every effort is taken to maintain the level of control necessary to preclude contamination in their controlled environments. Contamination most often is caused by workers in the cleanroom and/or by items brought into the cleanroom. The problems associated with keeping these rooms clean have not been easily solved.

Rigorous regulatory guidelines have been established, and continue to be developed, utilizing a variety of inter-related methodologies for operating cleanrooms in a manner best suited to exclude unwanted contaminants from the controlled environment. In adhering to these regulatory guidelines and assuring an acceptable environment in which to manufacture certain products, industries must be able to address known contamination with a documented control, which requires a cleaning regime that has been proven effective. Maintaining a cleaning system that is meaningful, manageable and defendable, however, becomes complex in production areas based on a multitude of variables.

One such variable that determines the effectiveness of a cleaning system is the ability to properly contact contaminants in a manner sufficient to neutralize or remove them. More specifically, a chemical agent capable of destroying the cells of contaminants needs to saturate and penetrate the cell walls over a specified contact time. Chemical agents are applied using various techniques, including using a sprayer, a mop, and/or a fogger. Although sprayers, mops with buckets and foggers have all been utilized in varying capacities and with varying success in cleanroom applications, the more of these separate components that are introduced into the controlled environment of a cleanroom, the greater the likelihood of introducing contaminants into the controlled environment.

Even when few components are introduced into a cleanroom, the likelihood of introducing contaminants along with the components increases every time a component must be removed and re-introduced into the controlled environment during the cleaning operation. For example, the use of a mop with a bucket results in "dirty water" mopping, which may actually contribute to the spread of contaminants. The bucket, therefore, must be routinely emptied and refilled. This not only increases the likelihood of introducing contaminants into the cleanroom, it also increases the volume of cleaning agents required to complete the cleaning operation.

In an attempt to address the above issues, at least one system has been developed that includes a sprayer, a sponge mop and a fogger all in one unit. This prior art system, illustrated in FIGS. 1 and 2, is offered by Veltek Associates, Inc. under the name CORE2CLEAN. The unit includes a re-sealable pressure vessel 2 for storing cleaning solutions, such as disinfectant, therein so as to protect the cleaning solution from contaminants when the unit is being used in a cleaning operation. The vessel 2 can be un-sealed by removing a vessel lid 4, at which point a cleaning solution may be placed in or removed from the vessel 2. The vessel 2 is autoclavable inside and out in the un-sealed configuration. After cleaning solution is placed in the vessel 2, it can be sealed from external contaminants by installing the vessel lid 4.

Cleaning solution can be dispensed from the sealed vessel 2 via the sprayer, sponge mop or fogger on an as-needed basis, thereby eliminating contamination due to the need to change dirty cleaning solutions during cleanroom washing, which also reduces the total volume of cleaning solution required to perform a cleaning operation. To provide the ability to dispense a continuous flow of cleaning solution in this unit, however, the system is operated by compressed gas, such as compressed air. The use of compressed air in a pressure vessel 2 creates many potential dangers arising from a potential sudden release of the pressure. Accordingly, safe operation of such a system requires implementation of various pressure regulating devices.

As illustrated in FIG. 1, the prior art system includes a pressure vessel 2 having a vessel lid 4, a handle 6, a first connection point 8, and a second connection point 10. The vessel lid 4 can be removed to access the inside of the vessel 2 to add or remove contents, such as cleaning solutions. The vessel lid 4 maintains an airtight seal in the vessel 2 when installed. The handle 6 is used to facilitate removal and installation of the vessel lid 4.

As illustrated in FIG. 2, the prior art system also includes a drain valve 12, an outlet regulator assembly 14, and an inlet regulator assembly 26. The drain valve 12 is located substantially at the bottom of the vessel 2 and is used to drain cleaning and rinsing solutions out of the vessel 2 when the vessel 2 is being cleaned. The outlet regulator assembly 14 is installed at the first connection point 8 and is used to dispense cleaning solution from the vessel using a cleaning applicator, such as a sprayer, sponge mop or fogger. The inlet regulator assembly 26 is installed at the second connection point 10 and is used to charge the vessel 2 with air pressure. The outlet regulator assembly 14 and the inlet regulator assembly 26 are removable from the vessel 2 so the vessel 2 may be properly autoclaved.

The first connection point 8 includes a dip tube assembly 16 that is in fluid communication with the bottom of the vessel 2 so that cleaning solution can be extracted therefrom. Because only the first connection point 8 includes a dip tube assembly 16 for extracting fluids from the bottom of the vessel 2, the outlet regulator assembly 14 and the inlet regulator assembly 26 cannot be interchangeably installed on the first connection point 8 and the second connection point 10. Accordingly, the outlet regulator assembly 14 can only be installed at the first connection point 8. Further, both the first connection point 8 and the second connection point 10 include internal check-type valves that are in the closed position to prevent fluid communication between the inside of the vessel 2 and the outside of the vessel 2 when the outlet regulator assembly 14 and the inlet regulator assembly 26 are not respectively installed therein.

As used herein, the term "fluid communication" includes a path by which liquids or gases may move between two or more structures. The term "gas communication" includes a path by which gases, such as air or steam, may move between two or more structures. Also herein, the terms "air" and "gas" are used interchangeably, unless otherwise apparent from the context.

The outlet regulator assembly 14 of the prior art system includes an outlet connector 18, an inlet connector 20, an outlet manual control valve 22, and an outlet pressure gauge 24. When using the system to dispense cleaning solution, cleaning applicators, such as a sprayer, sponge mop and fogger, are interchangeably connected to the outlet regulator assembly 14 at the outlet connector 18. With the cleaning applicator connected to the outlet regulator assembly 14, the outlet regulator assembly 14 is then installed on the vessel 2 at the first connection point 8 via the inlet connector 20 of the outlet regulator assembly 14. After the vessel 2 has been charged, a user may manually adjust the pressure with which the cleaning solution is dispensed from the vessel 2 by opening or closing the outlet manual control valve 22 as required until the desired pressure is observed on the outlet pressure gauge 24. Charging the vessel 2 is described in more detail below with reference to the inlet regulator assembly 26.

The inlet regulator assembly 26 of the prior art system includes an outlet connector 28, an inlet connector 30, an inlet manual control valve 32, a relief valve 34, an inlet pressure gauge 36, and a manual purge valve 38. To place a charge on the vessel 2, the inlet regulator assembly 26 is installed on the vessel 2 at the second connection point 10 via the outlet connector 28 of the inlet regulator assembly 26. With the inlet regulator assembly 26 installed on the vessel 2, a charging device (not shown), such as a pressurized tank or line, is then installed at the inlet connector 30 of the inlet regulator assembly 26. The user must then open the inlet manual control valve 32 to allow air pressure in the charging device to be transferred into the vessel 2. The user must manually adjust the air pressure in the vessel 2 by opening or closing the inlet manual control valve 32 as required until the desired pressure is observed on the inlet pressure gauge 36.

If the pressure inside the vessel 2 reaches a predetermined value, such as 100 psi, or greater at any point while the inlet regulator assembly 26 is installed on the vessel 2, the relief valve 34 will release some of the air pressure to prevent the air pressure within the vessel 2 from exceeding the predetermined value. Excess pressure can be released from the vessel 2 in this manner, however, only when the inlet regulator assembly 26 is installed on the vessel 2. There are no means by which to relieve excess pressure from the vessel 2 when the inlet regulator assembly 26 is not installed on the vessel 2.

The inlet regulator assembly 26 of the prior art system is also used to purge the vessel 2 of air to remove any pressure within the vessel 2. The vessel 2 may need to be purged, for example, before checking or servicing any part of the system, before loosening or removing the vessel lid 4, or after the user has concluded use of the system. To purge the system, the inlet regulator assembly 26 must be installed on the vessel 2 at the second connection point 10 via the outlet connector 28 of the inlet regulator assembly 26. There is fluid communication between the manual purge valve 38 and the vessel 2 whenever the inlet regulator assembly 26 is installed on the vessel 2 at the second connection point 10. Accordingly, the prior art system may be purged using inlet manual control valve 32, the manual purge valve 38, or a combination thereof, but the inlet regulator assembly 26 must be installed on the vessel 2 at the second connection point 10.

To purge the prior art system while the charging device is installed at the inlet connector 30 of the inlet regulator assembly 26, the inlet manual control valve 32 must be in the closed position so that air from the charging device is not continuously supplied to the vessel 2, thereby preventing proper purging. The inlet manual control valve 32 includes an orifice that is in fluid communication with the outside of the vessel 2 when the inlet manual control valve 32 is closed. Accordingly, air may escape from the vessel 2 via the orifice when the inlet manual control valve 32 is closed, thereby purging the vessel 2. The vessel 2 is therefore purged by closing the inlet manual control valve 32 if the charging device is installed in the inlet regulator assembly 26. The manual purge valve 38 may also be opened in this configuration to allow air within the vessel to escape therethrough, the manual purge valve 38 thereby operating simultaneously with the orifice of the inlet manual control valve 32 to purge the vessel.

The prior art system, however, is more likely to be purged with the charging device removed from the inlet connector 30 of the inlet regulator assembly 26. To purge the vessel 2 with the charging device removed from the inlet regulator assembly 26, the inlet manual control valve 32 may be in the open or closed position. The vessel 2 may be purged by placing the inlet manual control valve 32 in the closed position, thereby allowing air within the vessel 2 to escape through the orifice in the inlet manual control valve 32. The manual purge valve 38 may also be opened in this configuration to allow air within the vessel to escape therethrough, the manual purge valve 38 thereby operating simultaneously with the orifice of the inlet manual control valve 32 to purge the vessel. The vessel may also be purged by placing the inlet manual control valve 32 in the open position. With the inlet manual control valve 32 in the open position, air within the vessel 2 may not escape through the orifice in the inlet manual control valve 32. Accordingly, the manual purge valve 38 is opened to allow air to escape from the vessel 2 when the inlet manual control valve 32 is in the open position, thereby purging the vessel 2.

Thus, a manual purge valve 38 and inlet pressure gauge 36 must be disposed on the inlet regulator assembly 26 to purge the system. Accordingly, the inlet regulator assembly 26 must be installed on the vessel 2 of the prior art system to purge that system. This is not only an unnecessarily complicated configuration, it also poses certain safety risks.

Using the inlet manual control valve 32, the manual purge valve 38, or a combination thereof as described above, the subject valve(s) remain open until the user observes a pressure of zero (0) psi on the inlet pressure gauge 36 and can no longer hear air escaping the vessel 2. After the vessel 2 is purged, the inlet regulator assembly 26 is removed from the vessel 2 to allow the vessel 2 to be sterilized by a process such as autoclaving. Autoclaving includes utilizing high temperature steam in a sterilization process.

To autoclave the vessel, the vessel lid 4 must be removed and the drain valve 12 is opened to allow steam to pass through the vessel 2. The outlet regulator assembly 14 and the inlet regulator assembly 26 are removed from the vessel 2 during autoclaving because they are not autoclavable. The outlet regulator assembly 14 and the inlet regulator assembly 26 are not autoclavable because they are not configured to allow steam to pass therethrough and because their respective components 18-24 and 28-38 are not designed to withstand the high temperatures associated with autoclaving. Thus, the outlet connector 18, inlet connector 20, outlet manual control valve 22, and outlet pressure gauge 24 of the outlet regulator assembly 14 and the outlet connector 28, inlet connector 30, inlet manual control valve 32, relief valve 34, inlet pressure gauge 36, and manual purge valve 38 of the inlet regulator assembly 26 are all not autoclavable. These components, therefore, can trap bacteria therein, which will adversely affect a subsequent cleaning operation using the system, thereby reducing the reliability and control of the system. Accordingly, there is a present need for a system or effectively washing cleanrooms in which all of the components are autoclavable, and in which the steps of charging, operating, and purging the system are both simpler and safer.

SUMMARY OF THE INVENTION

In view of the foregoing, it is a non-limiting object of the present invention to provide an autoclavable bucketless cleaning system that includes an autoclavable vessel with an inside for storing fluid under pressure and with a first connection point and a second connection point disposed at an outside of the vessel, an autoclavable outlet regulator assembly for dispensing fluid from the vessel and removably connected to the vessel at the first connection point so as to be in fluid communication with the inside of the vessel, and an autoclavable inlet regulator assembly for pressurizing the vessel and removably connected to the vessel at the second connection point to be in fluid communication with the inside of the vessel.

It is another non-limiting object of the present invention to provide a method of performing a cleaning operation with an autoclavable bucketless cleaning system that includes placing a cleaning solution in an inside of an autoclavable vessel where the vessel includes a first connection point and a second connection point disposed at an outside of the vessel, removably connecting an autoclavable outlet regulator assembly on the vessel at the first connection point so the outlet regulator assembly is in fluid communication with the inside of the vessel, removably connecting an autoclavable inlet regulator assembly on the vessel at the second connection point so the inlet regulator assembly is in fluid communication with the inside of the vessel, pressurizing the inside of the vessel via the inlet regulator assembly, dispensing cleaning solution from the inside of the vessel via the outlet regulator assembly to clean a designated area, removing any pressurized gas that remains inside the vessel after the designated area is cleaned, removing any cleaning solution that remains inside the vessel after the designated area is cleaned, and autoclaving each of the vessel, the outlet regulator assembly, and the inlet regulator assembly.

These and other objects of the invention, as well as many of the intended advantages thereof, will become more readily apparent when reference is made to the following description, taken in conjunction with the accompanying drawings.

DETAILED DESCRIPTION OF EXEMPLARY EMBODIMENTS

Figure 1:
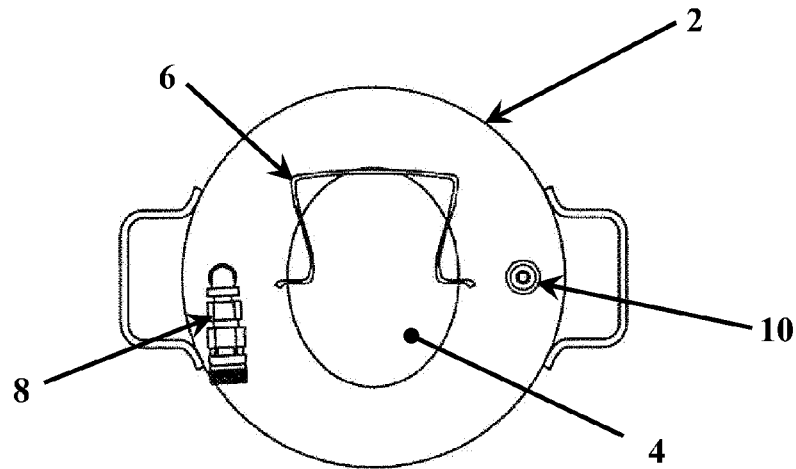
FIG. 1 shows a top view illustrating a pressure vessel of a prior art bucketless cleanroom washing system.

Many non-limiting aspects of the present invention can be better understood with reference to the following figures. The components in the figures are not necessarily to scale, emphasis instead being placed upon clearly illustrating the principles of the present invention. Moreover, in the figures, like reference numerals designate corresponding parts throughout the several views. Further, in describing the non-limiting aspects of the present invention illustrated in the figures, specific terminology is resorted to for the sake of clarity. Each specific term, however, is meant to include all technical equivalents that operate in a similar manner to accomplish a similar purpose. The present invention, therefore, is not limited to the specific terms so selected.

Figure 3:
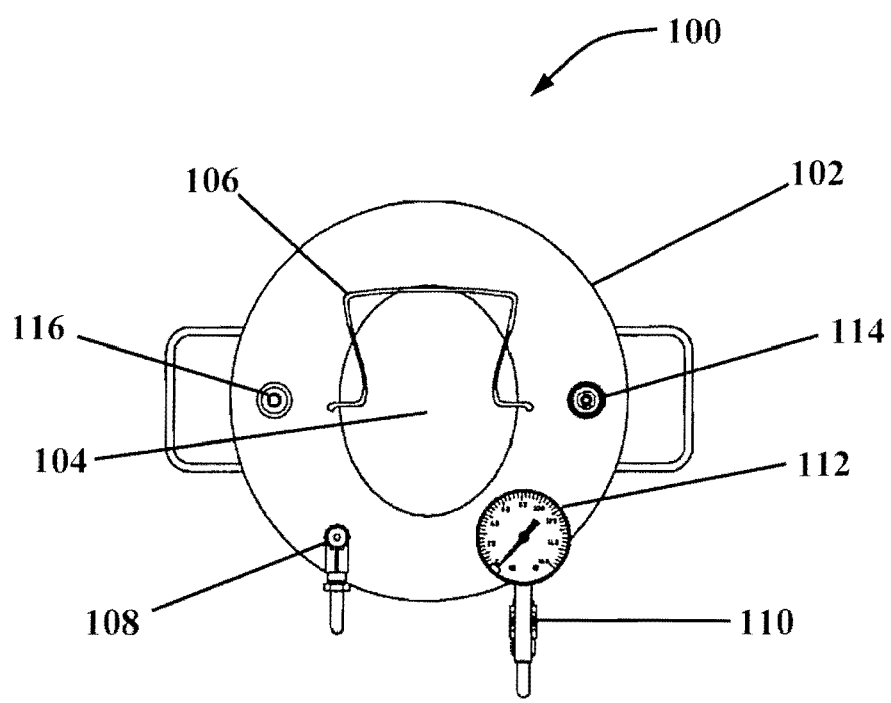
FIG. 3 shows a top view illustrating a pressure vessel in accordance with a non-limiting embodiment of the bucketless cleanroom washing system of the present invention.

Turning to the figures, FIG. 3 shows a top view illustrating a non-limiting embodiment of the autoclavable bucketless cleanroom washing system 100 of the present invention. The system 100 includes a re-sealable pressure vessel 102 having a vessel lid 104, a handle 106, a relief valve 108, a manual purge valve 110, a vessel pressure gauge 112, a first connection point 114, and a second connection point 116. The vessel lid 104 can be removed to access the inside of the vessel 102 to add or remove contents, such as cleaning solutions. The vessel lid 104 maintains an airtight seal in the vessel 102 when installed. The handle 106 is used to facilitate removal and installation of the vessel lid 104. The relief valve 108 automatically opens to relieve pressure from the vessel 102 when the pressure therein exceeds a predetermined value, for example 90 psi. The manual purge valve 110 is used to purge the vessel 102 of pressurized gas to remove any pressure inside the vessel 102. The vessel may need to be purged, for example, before checking or servicing any part of the system, before loosening or removing the vessel lid 104, or after the user has concluded use of the system. The vessel pressure gauge 112 allows a user to observe the pressure within the vessel 102 at all times.

The vessel lid 104 includes a handle 106 disposed thereon for removing and installing the vessel lid 104 on the vessel 102. The vessel lid 104 is sealably installed at the top of the vessel 102 with edges at the perimeter of the vessel lid 104 engaging corresponding edges in an opening at the top of the vessel 102 so as to create an airtight enclosure within the vessel 102 when installed. The airtight seal created by installing the vessel lid 104 in the vessel 102 allows fluids to be stored inside the vessel 102 and placed under pressure. The vessel lid 104 may be removed so that fluids can be placed in the vessel 102 through the opening at the top of the vessel 102. In an exemplary embodiment of the present invention, the vessel 102 is ASME rated to at least 90 psi when sealed.

The relief valve 108 remains closed until the pressure inside the vessel 102 exceeds a predetermined value, at which point the valve automatically opens to allow pressurized gas inside the vessel 102 to escape until the pressure inside the vessel 102 is at or below the predetermined value. The relief valve 108 is connectably disposed in the top of the vessel 102 and is in direct gas communication with the inside thereof. The relief valve 108 is normally in the closed position so that there is not gas communication between the inside of the vessel 102 and the outside of the vessel 102 via the relief valve 108. When the pressure within the vessel 102 exceeds the predetermined value, the relief valve 108 will open to allow gas communication between the inside of the vessel 102 and the outside of the vessel 102. The relief valve 108 may be preset to open at any pressure value above the pressure value that the vessel 102 is rated to safely contain, such as 90 psi.

The relief valve 108 may also include an exhaust tube connected thereto for directing any gas released from the relief valve 108 away from a user of the system 100.

The manual purge valve 110 is manually opened and closed. As illustrated in the exemplary embodiment of FIG. 4, the manual purge valve 110 is disposed at the top of the vessel 102 with a vessel pressure gauge 112 connectably disposed between the manual purge valve 110 and the vessel 102. The manual purge valve 110 and vessel pressure gauge 112 are in gas communication with the inside of the vessel 102 and with each other. In another exemplary embodiment of the system 100, the manual purge valve may be connectably disposed in the top of the vessel 102 at one location so as to be in direct gas communication with the inside of the vessel 102, and the vessel pressure gauge may be connectably disposed directly in the top of the vessel 102 in another location so as to be in direct gas communication with the inside of the vessel 102. The vessel pressure gauge 112 measures and displays the pressure within the vessel 102.

The manual purge valve 110 is normally in the closed position so that there is not gas communication between the inside of the vessel 102 and the outside of the vessel 102 via the manual purge valve 110. Because it is disposed between the manual purge valve 110 and the vessel 102, the vessel pressure gauge 112 is in direct gas communication with the inside of the vessel 102 even when the manual purge valve 110 is in the closed position. Thus, the vessel pressure gauge 112 continuously measures and displays the pressure within the vessel 102 regardless of whether the manual purge valve 110 is in the open or closed position and whether the outlet regulator assembly 120 and/or the inlet regulator assembly 136 are installed on the vessel 102. The manual purge valve 110 can be opened to reduce or remove pressure in the vessel 102, a process generally referred to as "purging" the vessel 102. The manual purge valve 110 may also include an exhaust tube connected thereto for directing any gas being released from the manual valve 110 away from a user of the system 100.

Figure 4:
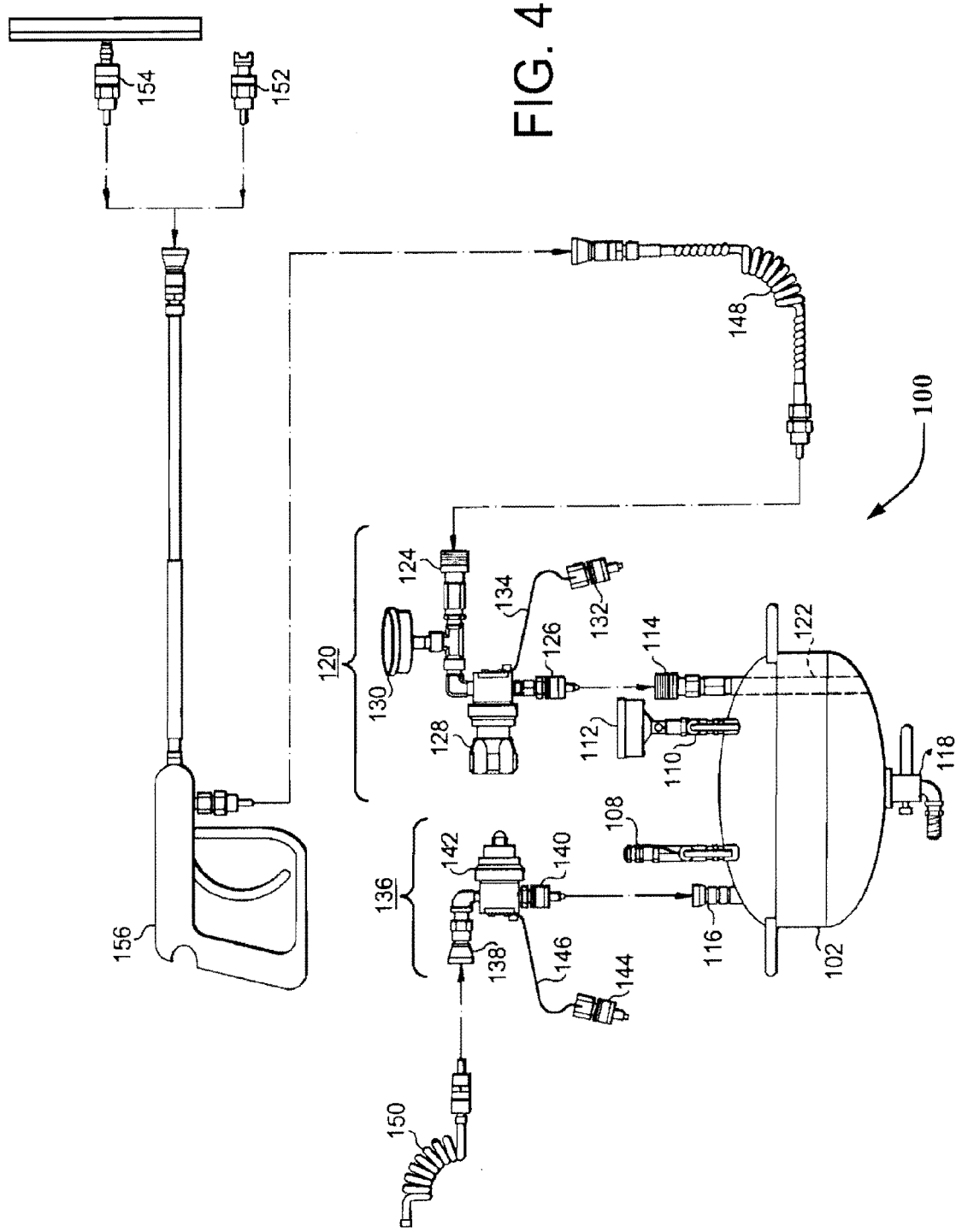
FIG. 4 is a side view of the bucketless cleanroom washing system illustrated in FIG. 3, including an inlet regulator assembly and an outlet regulator assembly.

As illustrated in FIG. 4, the system 100 also includes a drain valve 118, an outlet regulator assembly 120, and an inlet regulator assembly 136. The drain valve 118 is located substantially at the bottom of the vessel 102 and is used to drain the vessel 102 when the vessel 102 is cleaned. The outlet regulator assembly 120 is installed at the first connection point 114 and is used to dispense cleaning solution from the vessel using a cleaning applicator, such as a sprayer 152, sponge mop 154 or fogger (not shown). The inlet regulator assembly 136 is installed at the second connection point 116 and is used to charge the vessel 102 with gas to a predetermined pressure value.

The first connection point 114 includes a dip tube assembly 122 that is in fluid communication with the bottom of the vessel 102 so that cleaning solution can be extracted therefrom. Because only the first connection point 114 includes a dip tube assembly 122 for extracting fluids from the bottom of the vessel 102, the outlet regulator assembly 120 and the inlet regulator assembly 136 may not be interchangeably installed on the first connection point 114 and the second connection point 116. Accordingly, the outlet regulator assembly 120 may only be installed at the first connection point 114. Further, both the first connection point 114 and the second connection point 116 include internal check-type valves that are in the closed position to prevent fluid communication between the inside of the vessel 102 and the outside of the vessel 102 when the outlet regulator assembly 120 and the inlet regulator assembly 136 are not respectively installed therein. When the inlet connector 126 of the outlet regulator assembly 120 is installed at the first connection point 114, the check-valve in the first connection point 114 is opened so as to allow fluid communication between the vessel 102 and the outlet regulator assembly 120. When the outlet connector 140 of the inlet regulator assembly 136 is installed at the second connection point 116, the check-valve in the second connection point 116 is opened so as to allow fluid communication between the vessel 102 and the inlet regulator assembly 136.

In an exemplary embodiment of the present invention, the first connection point 114 may be keyed to only receive the inlet connector 126 of the outlet regulator assembly 120 to prevent mistakenly installing the outlet regulator assembly 120 at the second connection point 116 or installing the inlet regulator assembly 136 at the first connection point 114. Alternatively, the first connection point 114 and the second connection point 116 may be of different sizes to prevent mistakenly installing the outlet regulator assembly 120 at the second connection point 116 or installing the inlet regulator assembly 136 at the first connection point 114.

The outlet regulator assembly 120 of the system 100 includes an outlet connector 124, an inlet connector 126, an outlet metering valve 128, an outlet pressure gauge 130, an outlet autoclave stem 132, and a lanyard 134. The outlet connector 124 is disposed at one end of the outlet regulator assembly 120 and the inlet connector 126 is disposed at the other end of the outlet regulator assembly 120. The outlet metering valve 128 and the outlet pressure gauge 130 are positioned between the outlet connector 124 and the inlet connector 126. The outlet metering valve 128 is positioned adjacent to the inlet connector 126 and the outlet pressure gauge 130 is positioned between the outlet connector 124 and the outlet metering valve 128. The outlet connector 124, inlet connector 126, outlet metering valve 128, and outlet pressure gauge 130 are connectably joined so that each member of the outlet regulator assembly 120 is in fluid communication with each other member. The outlet pressure gauge 130 measures and displays the pressure between the outlet metering valve 128 and the outlet connector 124.

The outlet metering valve 128 is manually opened and closed using a flow control element, e.g., a valve handle, such that each incremental adjustment of the flow control element produces a substantially proportional change of the mass flow rate through the outlet metering valve 128. The outlet metering valve 128 of the present system 100 differs from the outlet manual control valve 22 of the prior art system because it allows more accurate control of flow rates. The outlet metering valve 128 of the outlet regulator assembly 120 is opened to allow fluid communication between the outlet connector 124 and the inlet connector 126 and closed to prevent fluid communication between the outlet connector 124 and the inlet connector 126, i.e., to stop cleaning solution from being dispensed from the vessel 102 via the outlet regulator assembly 120. The outlet metering valve 128 may be partially opened such that the amount of fluid communication between the outlet connector 124 and the inlet connector 126 corresponds to the amount the outlet metering valve 128 is opened, with a larger opening corresponding to a larger amount of fluid communication.

In the non-limiting embodiment of FIG. 4, the outlet connector 124 of the outlet regulator assembly 120 is a female quick disconnect that includes an internal check-type valve configured to be in the closed position when not connected to a corresponding male quick disconnect or autoclave stem. The inlet connector 126 of the outlet regulator assembly 120 is a male quick disconnect that is configured to be open at all times. Accordingly, when a corresponding male quick disconnect or autoclave stem is not installed at the outlet connector 126, there is no fluid communication through the outlet regulator assembly 120 due to the closed check-type valve in the outlet connector 124, i.e., fluid can enter the outlet regulator assembly 120 via the inlet connector 126 but it cannot exit the outlet regulator assembly 120 via the outlet connector 124, regardless of whether the outlet metering valve 128 is opened.

The outlet autoclave stem 132 mates with the outlet connector 124 of the outlet regulator assembly 120 so as to open the check-type valve in the outlet connector 124. This allows steam to pass through the outlet regulator assembly 120 during autoclaving, i.e., into the inlet connector 126 and out of the outlet connector 124. The outlet autoclave stem 132 is attached to the outlet regulator assembly 120 with the lanyard 134 so that the outlet autoclave stem 132 is not misplaced from the outlet regulator assembly 120 when not in use.

The inlet regulator assembly 136 of the system 100 includes an inlet connector 138, an outlet connector 140, a regulator valve 142, an inlet autoclave stem 144, and a lanyard 146. The inlet connector 138 is disposed at one end of the inlet regulator assembly 136 and the outlet connector 140 is disposed at the other end of the inlet regulator assembly 136. The regulator valve 142 is positioned between the inlet connector 138 and the outlet connector 140. The inlet connector 138, outlet connector 140, and regulator valve 142 are connectably joined so that each member of the inlet regulator assembly 136 is in fluid communication with each other member.

The regulator valve 142 remains open until the pressure inside the vessel 102 reaches a predetermined value, at which point the valve automatically closes to prevent more gas from entering the vessel 102, thereby preventing the pressure of the gas in the vessel 102 from rising to a dangerous value, i.e., above the pressure value that the vessel 102 is rated to contain. The regulator valve 142 of the inlet regulator assembly 136 is open to allow fluid communication between the inlet connector 138 and the outlet connector 140 until the pressure inside the vessel 102 reaches a predetermined value, at which point the regulator valve 142 will close to prevent fluid communication between the inlet connector 138 and the outlet connector 140. The regulator valve 142 is preset to close at a pressure value at or below the pressure value that the vessel 102 is rated to safely contain. The regulator valve 142 is used to fill the vessel 102 with pressurized gas, such as pressurized air. This process is generally referred to as "charging" the vessel 102.

In the non-limiting embodiment of FIG. 4, the inlet connector 138 of the inlet regulator assembly 136 is a female quick disconnect that includes an internal check-type valve configured to be in the closed position when not connected to a corresponding male quick disconnect or autoclave stem. The outlet connector 140 of the inlet regulator assembly 136 is a male quick disconnect that is configured to be open at all times. Accordingly, when a corresponding male quick disconnect or autoclave stem is not installed at the inlet connector 138, there is no fluid communication through the inlet regulator assembly 136 due to the closed check-type valve in the inlet connector 138, i.e., fluid can enter the inlet regulator assembly 136 via the outlet connector 140 but it cannot exit the inlet regulator assembly 136 via the inlet connector 138, regardless of whether the regulator valve 142 is opened. The regulator valve 142 may also prevent fluid from exiting the inlet regulator assembly 136 via the inlet connector 138 by being configured to function as a directional-type valve in addition to functioning as a regulator valve, thereby allowing fluid to flow through the inlet regulator assembly 142 only in a direction from the inlet connector 138 to the outlet connector 140.

The inlet autoclave stem 144 mates with the inlet connector 138 of the inlet regulator assembly 136 so as to open the check-type valve in the inlet connector 138. The inlet autoclave stem 144 is connected at the inlet connector 138 to allow steam to pass through the inlet regulator assembly 136 during autoclaving, i.e., into the inlet connector 138 and out of the outlet connector 140. The inlet autoclave stem 144 may be attached to the inlet regulator assembly 136 with the lanyard 146 so that the inlet autoclave stem 144 is not misplaced from the inlet regulator assembly 136 when not in use.

The above-described components of the system 100 may be utilized together to perform a cleaning operation of a cleanroom. An exemplary embodiment of a method in which the system 100 may be utilized in a cleaning operation is described hereinafter with reference to FIGS. 3 and 4. The method includes filling the vessel 102 with a cleaning solution and sealing the vessel 102; connecting a cleaning applicator to the outlet regulator assembly 120 and installing the outlet regulator assembly 120 on the vessel 102; installing the inlet regulator 136 on the vessel 102 and connecting a charging device to the inlet regulator assembly 136; placing a charge on the vessel 102; dispensing the cleaning solution using the cleaning applicator; purging the vessel 102 after dispensing the cleaning solution is completed; draining and rinsing the system; and autoclaving the entire system 100 after the vessel 102 has been purged. These functions and the order in which they are performed are exemplary and non-limiting, but are chosen as a preferred method for safe and efficient operation of the system 100.

To fill the vessel 102 with cleaning solution, the vessel lid 104 is removed using the handle 106. Before removing the vessel lid 104, ensure the vessel 102 has been purged as discussed below using the manual purge valve 110. A predetermined amount of cleaning fluid is then placed inside the vessel 102 via an opening in the top thereof. After cleaning solution is placed in the vessel 102, the vessel lid 104 is sealably installed in the vessel 102 so as to create an airtight chamber within the vessel 102 that includes the cleaning solution.

With the vessel 102 filled with cleaning solution, a cleaning applicator is connected to the outlet regulator assembly 120 at the outlet connector 124. The cleaning applicator may be connected to the outlet regulator assembly 120 using an extension piece 148, such as a high pressure coil hose assembly. The outlet autoclave stem 132 is not installed in the outlet connector 124 when the cleaning applicator is connected to the outlet regulator assembly 120 because a connection cannot be made with the outlet connector 124 when the outlet autoclave stem 132 is installed. With the cleaning applicator connected to the outlet regulator assembly 120, the outlet regulator assembly 120 is then installed on the vessel 102 at the first connection point 114 via the inlet connector 126 of the outlet regulator assembly 120. With the vessel 102 sealed and the outlet regulator assembly 120 installed on the vessel 102, a charge may be placed on the vessel 102. A charge is preferably not placed on the vessel 102 until after the outlet regulator assembly 120 is installed on the vessel 102 because making the above connections can be more difficult when the system is pressurized.

To place a charge on the vessel 102, the inlet regulator assembly 136 is installed on the vessel 102 at the second connection point 116 via the outlet connector 140 of the inlet regulator assembly 136. With the inlet regulator assembly 136 installed on the vessel 102, a charging device (not shown), such as a pressurized tank, is then connected to the inlet connector 138 of the inlet regulator assembly 136. The charging device may be connected to the inlet regulator assembly 136 using a charging hose 150, such as a high pressure coil hose assembly. The charging hose 150 is connected to the inlet regulator assembly 136 only after the inlet regulator assembly 136 is installed in the vessel 102 because the connection between the inlet regulator assembly 136 and the vessel 102 can more difficult to make when there is pressure within the inlet regulator assembly 136. The inlet autoclave stem 144 is not installed in the inlet connector 138 when the charging hose 150 is connected to the inlet regulator assembly 136 because a connection cannot be made with the inlet connector 138 when the inlet autoclave stem 144 is installed. When the charging hose 150 is installed in the inlet regulator assembly 136, the vessel 102 will automatically receive a predetermined amount of pressurized gas from the charging hose 150 until the pressure in the vessel 102 reaches a predetermined value, the predetermined value of pressure corresponding to the pressure at which the regulator valve 142 is set to close. Thus, a user just connects the charging hose 150 to the inlet regulator assembly 136 and the regulator valve 142 closes when the pressure inside the vessel 102 reaches the desired predetermined pressure value. In an exemplary embodiment of the present invention, the regulator valve 142 is set to close at 90 psi.

Figure 2:
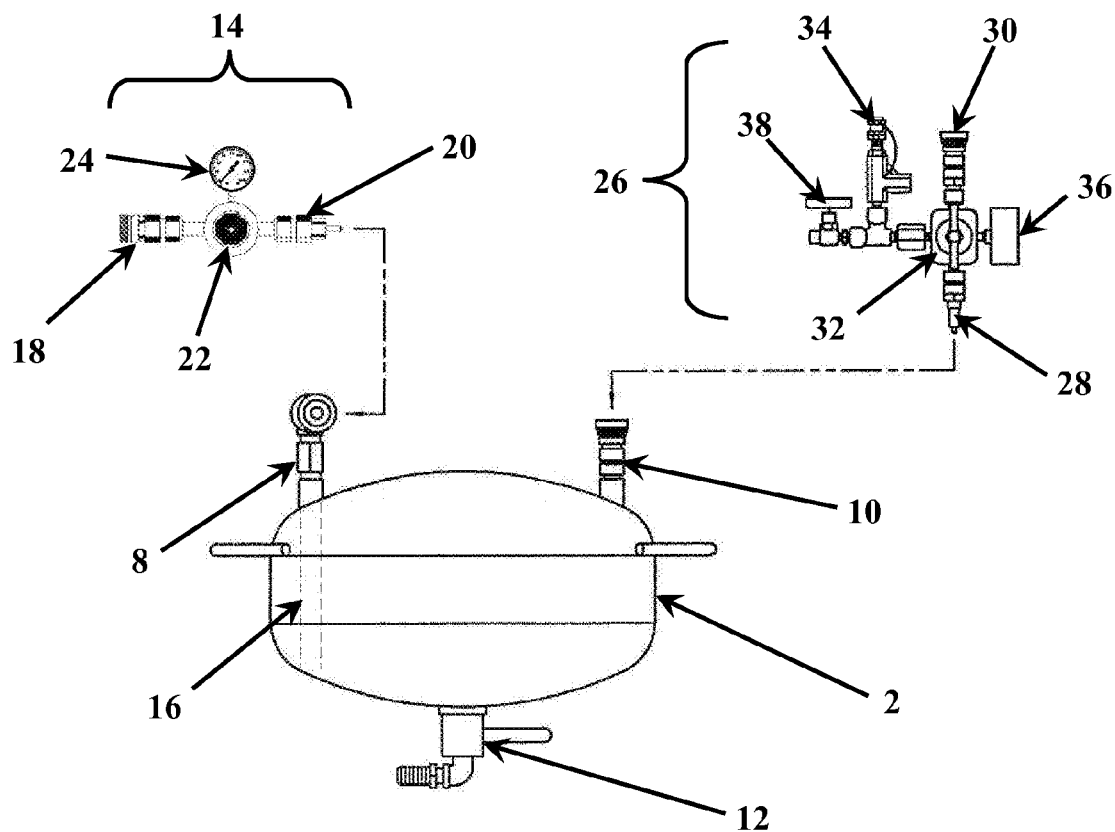
FIG. 2 is a side view of the prior art bucketless cleanroom washing system illustrated in FIG. 1, including an inlet regulator assembly and an outlet regulator assembly.

This is an improvement over the prior art system in which a user had to use an inlet manual control valve (see FIG. 2, element 30) to manually adjust the pressure placed in the vessel while observing the inlet pressure gauge (see FIG. 2, element 34) until the desired pressure is obtained. In the present invention, the desired pressure placed in the vessel 102 is obtained automatically via the regulator valve 142, thereby simplifying the charging process. Accordingly, this makes the system 100 more efficient in a cleaning operation by eliminating a step of manual adjustment. This also makes the system safer by allowing a regulator valve 142 to be set at a predetermined pressure that is at or below the pressure value that the vessel 102 is rated to safely contain and to prevent overflow. Thus, the need for an inlet manual control valve 32 and an inlet pressure gauge 36 on the inlet regulator assembly 26 as in the prior art system is eliminated.

If the regulator valve 142 malfunctions and does not close at the desired pressure, or if a user of the system bypasses the inlet regulator assembly 136 and tries to place a pressure in the vessel that exceeds the pressure value that the vessel 102 is rated to safely contain, the relief valve 108 disposed in the vessel 102 will open before the pressure reaches an unsafe value, thereby providing an extra level of safety in the system. By having the relief valve 108 disposed in the vessel 102, a user is protected from charging the vessel 102 to an unsafe pressure if the user bypasses the inlet regulator assembly 136. Also, a user is protected if the pressure inside the vessel 102 rises to unsafe values due to other factors, such as extreme temperature changes, when the inlet regulator assembly 136 is not installed in the vessel 102. Thus, the relief valve 108 provides a direct and immediate safety check on the pressure inside the vessel 102.

With a charge placed on the vessel 102, the cleaning solution can be dispensed from the vessel using the cleaning applicator that is connected to the outlet regulator assembly 120. To dispense cleaning solution using the cleaning applicator, the outlet metering valve 128 is opened until the desired dispensing pressure is obtained. Flow rate and particle size of the cleaning solution dispensed from the system 100 are adjusted by opening or closing the outlet metering valve 128 as required until the desired pressure is observed on the outlet pressure gauge 130. In an exemplary embodiment of the present invention, the outlet metering valve 128 is adjustable between 0 (zero) and 60 psi.

The flow rate at which the cleaning solution is dispensed from the vessel 102 can be determined using a chart listing various flow rates that correspond to valve handle positions of the outlet metering valve 128. The chart is based on the valve handle position and the pressure drop across the outlet metering valve 128. The position of the valve handle corresponds to the cross-sectional area of flow through the outlet metering valve 128. The pressure drop across the valve is measured by subtracting the pressure observed on the outlet pressure gauge 130 from the pressure observed on the vessel pressure gauge 112. The outlet metering valve 128 allows a user of the system 100 to accurately measure the volume of cleaning solution dispensed over a specific duration of a cleaning operation. Specifically, by observing the time that cleaning solution is dispensed with respect to the flow rate, the user may determine the volume of cleaning solution dispensed during a cleaning operation. This allows the user to accurately and conveniently determine how much fluid to place in the vessel 102 based on how long a cleaning operation is estimated to take.

The flow rate at which the cleaning solution is dispensed from the vessel 102 can also be determined using a chart listing the various flow rates produced based on the pressure with which fluid is dispensed and the size of the orifice of the cleaning applicator attached to the outlet regulator assembly 120. The pressure with which fluid is dispensed is observed on the outlet pressure gauge 130, and the orifice size may be predetermined or variable depending on the type of cleaning applicator used. Accordingly, by changing orifice sizes on the cleaning applicator and adjusting the pressure with which fluid is dispensed via the outlet metering valve 128, the user may determine the volume of cleaning solution dispensed during a cleaning operation. This allows the user to more accurately and conveniently determine how much fluid to place in the vessel 102 based on how long a cleaning operation is estimated to take.

The particle size at which the cleaning solution is dispensed from the vessel 102 can be determined using a chart listing the various particle sizes produced based on the pressure with which fluid is dispensed and the size of the orifice of the cleaning applicator, for example a sprayer 152 or a fogger. The dispensing pressure is observed on the outlet pressure gauge 130. Accordingly, by varying orifice sizes on the sprayer 152 or fogger and adjusting pressure via the outlet metering valve 128, various particle sizes can be produced using the sprayer 152 or fogger.

During a cleaning operation, cleaning applicators, such as a sprayer 152, sponge mop 154 and/or fogger, may be used interchangeably. The amount of cleaning solution dispensed can also be controlled using a standard trigger spray wand 156. The spray wand may be connected to the outlet regulator assembly via an extension hose 148. The sprayer 152, sponge mop 154 or fogger may be interchangeably connected at the end of the extension hose 148 or the spray wand 156 via quick disconnect connections. When a cleaning applicator is connected directly to the extension piece 148, the amount of cleaning solution dispensed is controlled by adjusting the outlet metering valve 128 as discussed above with respect to flow rates. The spray wand 156, however, adds an extra element of control by allowing the user to dispense cleaning solution by squeezing a trigger on the spray wand 156 and to stop the dispensing of cleaning solution by releasing the trigger of the spray wand 156. This added element of control over the amount of cleaning solution dispensed further increases the efficiency of the system 100.

When utilizing the sprayer 152 in a cleaning operation, the outlet metering valve 128 may be adjusted so that cleaning solution is dispensed at a desired pressure of 30 psi, as observed on the outlet pressure gauge 130. When utilizing the sponge mop 154 in a cleaning operation, the outlet metering valve 128 may be adjusted so that cleaning solution is dispensed at a desired pressure of 25 psi, as observed on the outlet pressure gauge 130. When using the fogger in a cleaning operation, the cleaning solution may be dispensed with a particle size between 5 and 50 microns.

Upon completion of the cleaning operation, pressure is manually relieved, or purged, from the system 100. Pressure is purged from the vessel 102 via the manual purge valve 110 disposed on the vessel 102. To purge the vessel 102, the manual purge valve 110 is opened and remains open until a pressure of 0 (zero) psi is observed on the vessel pressure gauge 112 and gas can no longer be heard escaping the vessel 102 through the manual purge valve 110. The vessel cannot be purged from the outlet regulator assembly 120 because there is a dip tube assembly 122 attached to the first connection point 114 that is in fluid communication with the bottom of the vessel 102 such that purging the vessel 102 at this location would result in expelling cleaning solution that may remain in the vessel 102. Because the manual purge valve 110 is at the top of the vessel 102, purging only releases gas. This step of purging the system 100 should always be implemented before opening the vessel 102, before checking or servicing any part of the system and before loosening or removing the vessel lid 104.

In purging the system, pressure should also be purged from within the outlet regulator assembly 120 and extension hose 148 via the spray wand 156. To purge the outlet regulator assembly 120 and extension hose 148, the outlet metering valve 128 is closed and the trigger of the spray wand 156 is squeezed to relieve the pressure contained between the spray wand 156 and the outlet regulator assembly 120. This will also expel any cleaning solution remaining in the outlet regulator assembly 120, extension piece 148 and/or spray wand 156. Accordingly, purging should take place outside of the cleanroom wherein the cleaning operation has been completed.

This is an improvement over the prior art system in which the inlet regulator assembly (see FIG. 2, element 26) had to be installed on the vessel (see FIG. 2, element 2) to purge the system. In the present invention, the vessel 102 can be purged without the inlet regulator assembly 136 being installed. This not only simplifies the purging process, but it makes the system 100 safer. For example, the vessel 102 can be purged at any time because the manual purge valve 110 and vessel pressure gauge 112 are disposed directly on the vessel 102 rather than on the inlet regulator assembly 136. This is of particular importance since the vessel 102 should be purged whenever the vessel lid 104 is to be removed. There may also be other circumstances in which the pressure within the vessel needs to be purged.

After the system 100 is purged, the vessel 102 may be rinsed. The vessel 102 is rinsed by removing the vessel lid 104 and placing the appropriate rinsing solutions in the vessel 102. After the vessel is rinsed, the drain valve 118 is opened to allow the rinsing solution to exit the vessel 102. The system 100 may also be charged and the rinsing solution dispensed through the sprayer, sponge mop and/or fogger as described above to rinse those components as well.

After the system 100 is rinsed, all of the components of the system may be autoclaved, including the vessel 102 and its integrated components, the entire outlet regulator assembly 120, the entire inlet regulator assembly 136, the extension pieces 148 and 150, the sprayer 152, the sponge mop 154, the fogger, and the spray wand 156. The integrated components of the vessel 102 include the vessel lid 104, the handle 106, the relief valve 108, the manual purge valve 110, the vessel pressure gauge 112, the first connection point 114, the second connection point 116, and the drain valve 118. The "entire" autoclavable outlet regulator assembly 120 includes the outlet connector 124, the inlet connector 126, the outlet metering valve 128, the outlet pressure gauge 130, the outlet autoclave stem 132, and the lanyard 134. The "entire" autoclavable inlet regulator assembly 136 includes the inlet connector 138, the outlet connector 140, the regulator valve 142, the inlet autoclave stem 144, and the lanyard 146. The outlet regulator assembly 120 and the inlet regulator assembly 136 may be installed on the vessel 102 when the system 100 is autoclaved.

Prior to autoclaving the vessel 102 and vessel's integrated components 104-118 with the entire outlet regulator assembly 120 and the entire inlet regulator assembly 136 installed on the vessel 102, the vessel lid 104 is removed from the vessel 102 and the drain valve 118 is opened so that steam may pass through the vessel 102 during autoclaving. The outlet autoclave stem 132 is installed at the outlet connector 124 of the outlet regulator assembly 120 to open the internal check-valve of the outlet connector 124 so that steam may pass through the outlet regulator assembly 120 during autoclaving. The outlet metering valve 128 is also opened. The inlet autoclave stem 144 is installed at the inlet connector 138 of the inlet regulator assembly 136 to open the internal check-valve of the inlet connector 138 so that steam may pass through the inlet regulator assembly 136 during autoclaving. The inlet regulator valve 142 is automatically opened when the vessel 102 is purged and will remain open during autoclaving. The vessel pressure gauge 112 may be sprayed to saturation with a sterilizing compound, for example, Sterile 70% USP Isopropyl Alcohol, prior to introducing it into the autoclave so as to further ensure sterilization thereof.

In another non-limiting exemplary method of autoclaving the system 100, the outlet regulator assembly 120 and the inlet regulator assembly 136 may be removed from the vessel 102 and autoclaved separate from the vessel 102. To autoclave the vessel 102 and the outlet regulator assembly 120 and the inlet regulator assembly 136 separately, autoclave stems (not shown) are installed in the first connection point 114 and the second connection point 116 of the vessel 102 to open the internal check-valves therein so that steam may pass through the first connection point 114 and the second connection point 116 during autoclaving. Autoclave stems 132 and 144 are also installed in the outlet regulator assembly 120 and the inlet regulator assembly 136. In the exemplary embodiment where autoclaving occurs with the outlet regulator assembly 120 and the inlet regulator assembly 136 installed on the vessel 102, the internal check-valves of the first connection point 114 and the second connection point 116 are opened respectively by the inlet connector 126 of the outlet regulator assembly 120 and the outlet connector 140 of the inlet regulator assembly 136.

Thus, the entire system 100 may be autoclaved, including the vessel 102, the vessel's integrated components 104-118, the entire outlet regulator assembly 120, the entire inlet regulator assembly 136, the extension pieces 148 and 150, the sprayer 152, the sponge mop 154, the fogger, and the spray wand 156. Autoclaving includes utilizing steam in a sterilization process. Accordingly, the entire system 100 may be placed in an autoclaving device, such as a machine capable of achieving elevated temperatures and pressures, to sterilize all of the components 102-156 of the system 100. The system may be autoclaved, for example, at 121° C. for 35 minutes.

It is important that the entire system 100 be autoclavable. Any components that are not autoclaved can trap bacteria, which can adversely effect any subsequent cleaning operation performed using the same components. This reduces the reliability and control of the system. Accordingly, the system 100 of the present invention is reliable and provides substantial control over contaminants by allowing all of the components to be autoclaved.

In addition, each of the relief valve 108, the manual purge valve 110, the vessel pressure gauge 112, the outlet regulator assembly 120, and the inlet regulator assembly 136 have separate and distinct benefits that contribute to the reliability and control of the present system 100. Accordingly, each of these components can be used alone or in any combination thereof to achieve the same or similar benefits.

The foregoing description and drawings should be considered as illustrative only of the principles of the invention. The invention may be configured in a variety of shapes and sizes and is not intended to be limited by the preferred embodiment. Numerous applications of the invention will readily occur to those skilled in the art. Therefore, it is not desired to limit the invention to the specific examples disclosed or the exact construction and method of operation shown and described. Rather, all suitable modifications and equivalents may be resorted to, falling within the scope of the invention.

What is claimed is:

1. An autoclavable bucketless cleaning system comprising:
   a vessel with an inside for storing fluid under pressure, the vessel including a first connection point and a second connection point disposed at an outside of the vessel;
   an outlet regulator assembly for dispensing fluid from the vessel, the outlet regulator assembly being removably connected to the vessel at the first connection point so as to be in fluid communication with the inside of the vessel, the outlet regulator assembly comprising an outlet connector with an internal check-type valve configured to be in a closed position when not connected;
   an outlet autoclave stem for installing in the check-type valve of the outlet regulator assembly so that steam may pass through the outlet regulator assembly during autoclaving;
   an inlet regulator assembly for pressurizing the vessel, the inlet regulator assembly being removably connected to the vessel at the second connection point to be in fluid communication with the inside of the vessel, the inlet regulator assembly comprising an inlet connector with an internal check-type valve configured to be in a closed position when not connected; and
   an inlet autoclave stem for installing in the check-type value of the inlet regulator assembly so that steam may pass through the inlet regulator assembly during autoclaving.

2. The cleaning system of claim 1, wherein the vessel includes a relief valve attached at the outside of the vessel and in direct fluid communication with the inside of the vessel.

3. The cleaning system of claim 1, wherein the vessel includes a purge valve attached at the outside of the vessel and in direct fluid communication with the inside of the vessel.

4. The cleaning system of claim 3, wherein a pressure gauge is disposed between the purge valve and the vessel and in fluid communication with both the purge valve and the vessel.

5. The cleaning system of claim 1, wherein the vessel includes a pressure gauge attached at the outside of the vessel and in direct fluid communication with the inside of the vessel.

6. The cleaning system of claim 1, wherein the outlet regulator assembly includes an autoclavable metering valve that may be opened and closed by adjusting a flow control element such that each incremental adjustment of the flow control element produces a substantially proportional change of the mass flow rate through the metering valve.

7. The cleaning system of claim 6, wherein the outlet regulator assembly includes an autoclavable pressure gauge for measuring and displaying the pressure within the outlet regulator assembly on a side of the metering valve that is opposite to a side at which the outlet regulator assembly is installed on the vessel.

8. The cleaning system of claim 1, wherein the inlet regulator assembly includes an autoclavable regulator valve that remains open while pressurizing the vessel until a pressure inside the vessel reaches a predetermined value, at which point the regulator valve automatically closes to prevent more pressure from entering the vessel.

9. A method of autoclaving a bucketless cleaning system, the method comprising:
   placing a cleaning solution in an inside of a vessel, the vessel including a first connection point and a second connection point disposed at an outside of the vessel;
   removably connecting an outlet regulator assembly on the vessel at the first connection point so the outlet regulator assembly is in fluid communication with the inside of the vessel, the outlet regulator assembly comprising an outlet connector with an internal check-type valve configured to be in the closed position when not connected;
   removably connecting an inlet regulator assembly on the vessel at the second connection point so the inlet regulator assembly is in fluid communication with the inside of the vessel, the inlet regulator assembly comprising an inlet connector with an internal check-type valve configured to be in the closed position when not connected;
   installing an outlet autoclave stem in the outlet regulator assembly so that steam may pass through the outlet regulator assembly; and
   installing an inlet autoclave stem in the inlet regulator so that steam may pass through the inlet regulator assembly; and
   autoclaving each of the vessel, the outlet regulator assembly, and the inlet regulator assembly.

10. The method of claim 9, wherein the step of pressurizing the inside of the vessel includes connecting a charging device to the inlet regulator assembly such that an autoclavable regulator valve in the inlet regulator assembly automatically closes to prevent more pressure from entering the vessel when a pressure in the vessel reaches a predetermined value.

11. The method of claim 9, wherein the step of pressurizing the inside of the vessel is not performed via the inlet regulator assembly and an autoclavable relief valve disposed in direct fluid communication with the inside of the vessel remains closed until a pressure inside the vessel exceeds a predetermined value, at which point the relief valve automatically opens to allow at least some pressure inside the vessel to escape until the pressure remaining inside the vessel is at or below the predetermined value.

12. The method of claim 9, wherein the step of dispensing cleaning solution includes opening an autoclavable metering valve in the outlet regulator assembly by adjusting a flow control element such that each incremental adjustment of the flow control element produces a substantially proportional change of the mass flow rate through the metering valve.

13. The method of claim 9, wherein the step of dispensing cleaning solution includes interchangeably connecting an autoclavable sprayer, sponge mop, or fogger to the outlet regulator assembly for dispensing cleaning solution therethrough.

14. The method of claim 9, wherein the step of removing any pressurized gas that remains inside the vessel includes opening an autoclavable purge valve that is attached at the outside of the vessel and in direct fluid communication with the inside of the vessel.

15. The method of claim 9, wherein the step of removing any pressurized gas that remains inside the vessel includes leaving the purge valve open until a pressure gauge disposed between and in fluid communication with the purge valve and the vessel measures and displays 0 psi.

16. The method of claim 9, wherein the step of removing any cleaning solution that remains inside the vessel includes opening an autoclavable drain valve that is disposed at the bottom of the vessel and in direct fluid communication with the inside of the vessel.

17. The method of claim 9, wherein the step of autoclaving includes,
removing a lid from the vessel and opening a drain valve at the bottom of the vessel so that steam may pass through the vessel;
disconnecting the outlet regulator assembly from the vessel;
installing a first connection point autoclave stem in the first connection point so that steam may pass through the first connection point;
disconnecting the inlet regulator assembly from the vessel;
installing a second connection point autoclave stem in the second connection point so that steam may pass through the second connection point.

18. The method of claim 9, further comprising:
pressurizing the inside of the vessel via the inlet regulator assembly;
dispensing cleaning solution from the inside of the vessel via the outlet regulator assembly to clean a designated area;
removing any pressurized gas that remains inside the vessel after the designated area is cleaned; and
removing any cleaning solution that remains inside the vessel after the designated area is cleaned.

\* \* \* \* \*